United States Patent [19]

Ogura et al.

[11] 4,025,622

[45] May 24, 1977

[54] NOVEL SUGAR UREIDE AND THIOUREIDE DERIVATIVES

[75] Inventors: Haruo Ogura; Hiroshi Takahashi, both of Tokyo, Japan

[73] Assignee: Haruo Ogura, Tokyo, Japan

[22] Filed: Feb. 26, 1975

[21] Appl. No.: 553,121

[30] Foreign Application Priority Data

Mar. 6, 1974 Japan .............................. 49-25108
Sept. 30, 1974 Japan .......................... 49-111631

[52] U.S. Cl. .................................. 424/180; 536/18; 536/22
[51] Int. Cl.² ..................... A61K 31/13; C07H 5/04
[58] Field of Search ................ 260/211 R, 211.5 R; 424/180; 536/18, 22

[56] References Cited

UNITED STATES PATENTS

| 2,612,497 | 9/1952 | Meijer | 260/211.5 R |
|---|---|---|---|
| 2,967,859 | 1/1961 | Osipow et al. | 260/211.5 R |
| 3,027,364 | 3/1962 | Knoevenagel | 260/211.5 R |
| 3,135,748 | 6/1964 | Sheehan | 260/465.5 R |
| 3,149,033 | 9/1964 | Clark | 260/211.5 R |
| 3,158,598 | 11/1964 | Morel | 260/211.5 R |

*Primary Examiner*—Johnnie R. Brown
*Attorney, Agent, or Firm*—Larson, Taylor and Hinds

[57] ABSTRACT

Novel sugar ureide and thioureide derivatives are provided by this invention, which exhibit certain antibacterial activity against a variety of gram-positive and gram-negative bacteria and useful in therapeutic treatment of bacterial infections. The compounds have the formula

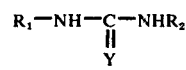

wherein $R_1$ is a monovalent residue of aldose, aldonic acid and their 2-amino derivatives, $R_2$ is an aralkyl, heterocyclic, sulfamoylaryl, $R_3CONH$ or $R_4NH-$ where $R_3$ is a heterocyclic and $R_4$ is an aryl group and Y is oxygen or sulfur atom, which are prepared by reacting an isocyanate or isothiocyanate of the formula $R_1NC=Y$ with an amino compound of the formula $R_2NH_2$.

18 Claims, No Drawings

NOVEL SUGAR UREIDE AND THIOUREIDE DERIVATIVES

This invention relates to novel sugar ureide and thioureide derivatives which are useful in the therapeutic treatment of infections by gram-positive and gram-negative bacteria. This invention further relates to a process for the preparation of the new derivatives, pharmaceutical compositions containing them and a method for the therapeutic treatment of bacterial infections.

It has now been found that certain novel sugar ureide and thioureide derivatives, as hereinafter defined, possess useful therapeutic activity against bacterial infections, as evidenced, for example, by in vitro tests.

According to this invention, therefore, there are provided as novel compounds sugar ureide and thioureide derivatives of the general formula:

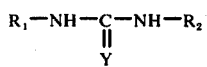

wherein $R_1$ represents a monovalent residue of aldose or 2-aminoaldose from which the hemiacetal-hydroxyl group has been removed and of which the alcoholic hydroxyl groups have been protected or a monovalent residue of aldonic acid or 2-aminoaldonic acid from which the hydroxyl group in the carboxyl group has been removed and of which the alcoholic hydroxyl groups have been protected; $R_2$ represents an unsubstituted or substituted aralkyl group, an unsubstituted or substituted and/or condensed heterocyclic group, a N-heterocylic-substituted sulfamoyl aryl group, a group $R_3CONM-$ wherein $R_3$ represents an unsubstituted or substituted heterocyclic group or a group $R_4NH-$ wherein $R_4$ represents an unsubstituted or substituted aryl group; and Y represents an atom of oxygen or sulfur.

The group $R_1$ may be a monovalent residue as above-defined, which was derived from any of aldose, 2-aminoaldose, aldonic acid and 2-amino-aldonic acid. Thus, typical examples of the group $R_1$ are OH-protected glycosyl and 2-aminoglycosyl groups such as glucosyl, arabinosyl, ribosyl, xylosyl, galactosyl and 2-amino-2-deoxyglucosyl groups and the corresponding glyconyl and 2-amino-deoxyglyconyl groups. In most cases, such a monovalent aldose or 2-aminoaldose residue is preferably in pyranosyl or furanosyl form, whereas a monovalent residue derived from aldonic acid or 2-amino-aldonic acid is preferably in linear form.

The group $R_2$ may be any of a wide variety of groups as above defined. Thus, for example, it may be an unsubstituted or substituted aralkyl group such as benzyl, 2-phenyl-1-carboxyl-ethyl, 4-sulfamoylbenzyl, (3-carboxy-2,2-dimethylpenam-6-yl-aminocarbonyl) benzyl, (4-carboxy-3-methyl-3-cephem-7-yl-aminocarbonyl)-benzyl and (4-carboxy-3-acetyloxymethyl- 3-cephem-7-yl-aminocarbonyl)benzyl; an unsubstituted or substituted and/or condensed heterocyclic group such as 2-pyridyl, 2-benzimidazolyl, 2-benzothiazolyl, 5-pyrazolyl, 5-(N-phenyl-4-carbamoyl)pyrazolyl, 5-(N-phenyl-4-ethoxycarbonyl)pyrazolyl, 6-pyrimidinyl, 6-(1,3-dimethyl-2,4-dioxo)pyrimidinyl, 6-penicillayl and 3-phenacyl-6-penicillanyl; a N-heterocyclic-substituted sulfamoyl aryl group such as 4-(N-3,4-dimethylisoxazolyl)sulfamoylphenyl, 4-(N-2,6-dimethyl-4-pyrimidyl)sulfamoylphenyl, 4-(N-2-pyrimidyl)-sulfamoylphenyl and 4-(N-2-thiazolyl)-sulfamoylphenyl; isonicotinoylamino; and p-nitroanilino and 2,4-dinitroanilino groups.

Specific examples of the sugar ureide and thioureide derivatives according to this invention are:
α-(2,3,4,6-Tetra-O-acetyl-D-glucopyranosyl thioureido) benzylpenicillin and triethylammonium salt thereof;
α-(2,3,4-Tri-O-acetyl-D-arabinopyranosylthioureido) benzylpenicillin and triethylammonium salt thereof;
α-(2,3,4,5,6-Penta-O-acetyl-D-gluconylthioureido) benzylpenicillin and triethylammonium salt thereof;
7-[D-α-(2,3,4,5,6-penta-Oacetyl-D-gluconylthioureido)-phenylacetamido]-3-methyl-3-cephem-4-carboxylic acid;
1-(2,3,4,6-Tetra-O-acetyl-β-D-glucopyranosyl)-3-benzyl-2-thiourea;
1-(2,3,4,6-Tetra-O-acetyl-β-D-glucopyranosyl)3-(benzimidazol-2-yl)-2-thiourea;
1-(2,3,4,6-Tetra-O-acetyl-β-D-glucopyranosyl)3-(benzothiazol-2-yl)-2-thiourea;
1-(4-Pyridylcarbonyl)-4-(2,3,4,5-tetra-O-acetyl-β-D-glucopyranosyl)-semicarbazide;
1-(2,3,4,6-Tetra-O-acetyl-β-D-glucopyranosyl)3-(1,3-dimethylpyrimidin-2,4-dione-6-yl)-2-thiourea;
6-(2,3,4,6-Tetra-O-acetyl-β-D-glucopyranosylthioureido) penicillanic acid and its triethylammonium salt;
1-(2,3,4-Tri-O-acetyl-α-D-arabinopyranosyl)-3-(benzothiazol-2-yl)-2-thiourea;
6-(2,3,4-Tri-O-acetyl-α-D-arabinopyranosylthioureido) penicillanic acid and its triethylammonium salt;
1-(2,3,4,6-Tetra-O-acetyl-β-D-glucopyranosyl)-3-(2,3-dimethyl-1-phenyl-3-pyrazolin-5-one-4-yl)-2-thiourea;
1-(2,3,4-Tri-O acetyl-α-D-arabinopyranosyl)-3-(2,3-dimethyl-1-phenyl-3-pyrazolin-5-one-4-yl)-2-urea;
1-(2,3,4,5,6-Penta-O-yl-D-gkycibtk-3-(benzothiazol-2-yl)-2-thiourea;
6-(2,3,4,5,6-Penta-O-acetyl-D-gluconylthioureido) penicillanic acid and its penacyl ester;
1-(2,3,4,5,6-Penta-O-acetyl-D-gluconyl)-3-(β-carboxy phenetyl)-2-thiourea;
1-Phenyl-4-ethoxycarbonyl-5-(2,3,4,5,6-penta-O-acetyl-D-gluconylthioureido)pyrazole;
2-(2,3,4,5,6-Penta-O-acetyl-D-gluconylthioureido) pyridine;
1-Phenyl-4-carbamoyl-5-(2,3,4,5,6-penta-O-acetyl-D-gluconylthioureido) pyrazole;
1-(4-Pyridylcarbonyl)-4-(2,3,4,5,6-penta-O-acetyl-D-gluconyl)thiosemicarbazide;
4-(2,3,4,5,6-Penta-O-acetyl-D-gluconylthioureido)-phenyl-N'-(3,4-dimethyl-5-isoxazolyl)-sulfonamide;
4-(2,3,4,5,6-Penta-O-acetyl-D-gluconylthioureido)-phenyl-N'-(2,6-dimethyl-4-pyrimidyl)-sulfonamide;
4-(2,3,4,5,6-Penta-O-acetyl-D-gluconylthioureido)-phenyl-N'-(2-pyrimidyl)-sulfonamide;
4-(2,3,4,5,6-Penta-O-acetyl-D-gluconylthioureido)-phenyl-N'-(2-thiazolyl)-sulfonamide; and
4-(2,3,4,5,6-Penta-O-acetyl-D-gluconylthioureidomethyl)-phenyl-sulfonamide.

Particularly preferred compounds according to this invention, in view of their activity, are α-(2,3,4,6-tetra-O-acetyl-D-glucopyranosyl-thioureido) benzylpenicillin and triethylammonium salt thereof, α-(2,3,4-tri-O- acetyl-D-arabinopyranosylthioureido) benzylpenicillin and triethylammonium salt thereof, α-(2,3,4,5,6-penta-O-acetyl-D-gluconyl-thioureido) benzylpenicillin and 7-[D-α-(2,3,4,5,6-penta-O-acetyl-D-gluconylthioureido)-phenylacetamido]-3-methyl-3-cephem-4-carboxylic acid.

The novel sugar ureide and thioureide derivatives according to this invention have been shown to exhibit certain antibacterial activity against a variety of gram-positive and gram-negative bacteria.

According to a further feature of this invention, therefore, there is provided a pharmaceutical composition comprising a sugar ureide or thioureide derivative according to this invention in association with a pharmaceutical carrier or diluent.

The nature of the composition and the pharmaceutical carrier or diluent will, of course, be dependent upon the route of administration, e.g. orally or parenterally. In general, the compositions will be in a form suitable for oral administration. Thus, the composition may be in the form of capsule, tablet, powder, granule and others.

This invention also includes within its scope a method for the therapeutic treatment of bacterial infections which comprises administering to a patient infected with gram-positive or gram-negative bacteria a therapeutically effective amount (e.g. 1–3 g/day), at suitable intervals, of a sugar ureide or thioureide derivative according to this invention.

The minimum inhibitory concentration (mcg/ml) of a variety of the sugar ureide and thioureide derivatives according to this invention against various bacteria was determined in accordance with a standard serial dilution method using as medium Brain heart in infusion broth (Difco) at 37° C, the determination being made after 24 hours incubation. The results are shown in Table 1 together with the results of test for ampicillin as reference. LDo value of certain specific compounds for mice by oral administration is also shown in Table 1.

The novel sugar ureide and thioureide derivatives according to this invention are prepared in a single stage by the addition-reaction of an isocyanate or isothiocyanate of aldose or aldonic acid or of 2-amino derivative thereof with an amino compound.

According to a further feature of this invention, therefore, there is provided a process of the preparation of sugar ureide and thioureide derivatives of the general formula:

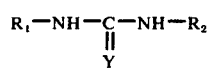    I wherein $R_1$, $R_2$ and Y have the meanings defined above which comprises reacting a compound selected from the group consisting of isocyanates and isothiocyanates of the general formula:

$$R_1NC=Y \qquad II$$

wherein $R_1$ and Y have the meanings defined above with an amino compound of the general formula:

$$R_2NH_2 \qquad III$$

wherein $R_2$ has the meaning defined above.

In carrying out the process according to this invention, the reaction between the compounds of the formulae II and III may be effected under anhydrous conditions, preferably in a non-polar solvent, for example hydrocarbons such as benzene, toluene, xylene and mixtures thereof and others such as tetrahydrofuran. If the compounds of the formula III are sparingly soluble in such a non-polar solvent, then the reaction may preferably be carried out in the coexistence of a secondary or tertiary amine such as dimethylformamide, diethylamine, triethylamine, piperidine, morpholine, pyridine and quinoline.

Satisfactory results may usually be obtained by reacting together the compounds II and III in equimolar proportions. Preferably, the reaction may be carried out at a temperature of 60°–200° C and usually under heating on water bath or under reflux on oil bath. The reaction time may depend upon the nature of the reactants and usually may vary from 20 minutes to 3 days. It is possible to use thin-layer chromatography for determining the completion of the reaction.

As the compounds of the formula II, there may be used any of isocyanate and isothiocyanate derivatives of aldose and aldonic acid. Typical examples of include glucose, arabinose, ribose, xylose, galactose and glucosamine and those of aldonic acid include aldonic acid corresponding to glucose, arabinose, ribose, xylose,

TABLE 1

| | MIC (mcg/ml) | | | | | | | |
|---|---|---|---|---|---|---|---|---|
| Compound (Example No.) | Staphylococcus aureus 209 P | Staphylococcus aureus No. 26 | Salmonella typhi O-901-W | Klebsiella pneumoniae | Escherichia coli IAM-1264 | Pseudomonas aeruginosa IAM-1007 | Proteus vulgaris OX 19 | LDo mg/kg |
| Inoculum size | 3.8×10⁵ | 2.3×10⁵ | 3.5×10⁵ | 1.3×10⁵ | 1.9×10⁵ | 1.3×10⁵ | 1.2×10⁵ | |
| 10 | 3.12 | 100 | 6.25 | 50 | 50 | 200 | >100 | >1000 |
| 13 | 3.12 | >100 | >100 | >100 | >100 | >100 | 25 | >1000 |
| 17 | 0.78 | >100 | 50 | >100 | >100 | >100 | 1.56 | >1000 |
| 28 | 12.5 | | >100 | >100 | >100 | >100 | 100 | >1000 |
| Ampicillin (Reference) | 0.1 | >100 | 0.39 | 1.56 | 3.12 | >100 | 100 | >1000 | galactose and glucosamine.

For isocyanate and isothiocyanate derivatives of aldose, the aldose residue is, in most cases, present in pyranosyl or furanosyl form. On the other hand, for isocyanate and isothiocyanate derivatives of aldonic acid, the aldonic acid residue may be present in open-chain, pyranosyl or furanosyl form, the open-chain form being predominant.

The alcoholic hydroxyl groups in the aldose or aldonic acid residue of the compounds of the formula II may be protected by a variety of OH-protecting groups known per se, for examle acetyl, benzoyl, benzyl, isopropylidene, benzylidene and cyclohexylidene groups, the most preferred group being acetyl.

Of the compounds of the formula II, those in which $R_1$ is a monovalent residue of aldonic acid are all novel compounds as such and may, for example, be prepared by chlorinating aldonic acid, of which alcoholic hydroxyl groups have been protected, with thionyl chloride, phosphorus trichloride, phosphorus pentachloride and the like followed by reacting the acid chloride thus formed with silver cyanate or thiocyanate.

As the compounds of the formula III, there may be used a wide variety of amino compounds having a primary or secondary amino group. Among others, typical examples of the compounds of the formula III include benzylamine, 2-aminobenzimidazole, 2-aminobenzothiazole, L-phenylalanine, N-phenyl-5-aminopyrazol-4-carboxylic acid amide, N-phenyl-5-aminopyrazol-4-carboxylic acid ethyl ester, 2-aminopyridine, isonicotinic acid hydrazide, p-nitrophenylhydrazine, 2,4-dinitrophenylhydrazine, 6-amino-1,3-dimethyluracil, 6-amino-penicillanic acid, phenacyl 6-aminopenicillanate, ampicillin (α-aminobenzylpenicillin), 4-aminoantipyrine (4-amino-2,3-dimethyl-1-phenyl-5-pyrazolone), cephalexin (7-(D-α-aminophenylacetamido)-3-methyl-3-1 cephem-4-carboxylic acid) and cephaloglicine (7-(D-α-aminophenylacetamido)-3-acetoxymethyl-3-cephem-4-carboxylic acid). Sulfamine compounds such as sulfisoxazole, sulfisomidin, sulfadiazine, sulfathiazole and homosulfamine and guanizine compounds such as buformin and phenformin may also be used.

After the reaction between the compounds of the formulae II and III has been completed, the reaction mixture may be treated in a conventional manner to isolate desired product therefrom. Purification of the product may also be carried out by a conventional technique, typically by recrystallization from an organic solvent, e.g. methanol and ethanol.

This invention is now illustrated, but not limited, by the following Examples.

EXAMPLE 1

1-(2,3,4,6-Tetra-O-acetyl-β-D-glucopyranosyl)-3-benzyl-2-thiourea

To 10 ml of anhydrous xylene were added 390 mg (1 mmol) of 2,3,4,6-tetra-O-acetyl-D-glucopyranosyl isothiocyanate and then slowly added 110 mg (1 mmol) of benzylamine (MW 107) under ice-cooling and stirring over 30 minutes. The mixture was then stirred at room temperature for 1.5 hours, during which crystals were deposited and then filtered off. Recrystallization from ethanol gave colourless needles melting between 126° and 128° C (uncorrected). Yield: 198 mg (40%).

IR $\nu_{max}^{KBr}$ cm$^{-1}$ 3300 (—NH), 1740 (COOCH$_3$), 720, 695 (phenyl).

Elementary analysis:
$C_{22}H_{28}O_9N_2S$ requires: C, 53.22; H, 5.68; N, 5.64%.
Found: C, 53.20; H, 5.65; N, 5.60%.

EXAMPLE 2

1-(2,3,4,6-Tetra-O-acetyl-β-D-glucopyranosyl)-3-(benzimidazol-2-yl)-2-thiourea

To 10 ml of anhydrous xylene were added 390 mg (1 mmol) of 2,3,4,6-tetra-O-acetyl-D-glucopyranosyl isothiocyanate and 135 mg (1 mmol) of 2-aminobenzimidazole (MW 133) and the mixture was heated at 100° C for 1 hour and allowed to cool to room temperature. Crystals formed were filtered off and recrystallized from methanol to give colourless needles melting between 162° and 165° C (uncorrected). Yield: 245 mg (47%).

IR $\nu_{max}^{KBr}$ cm$^{-1}$: 3350 (—NH), 1740 (COOCH$_3$), 1590, 740 (phenyl).

Elementary analysis:
$C_{22}H_{26}O_9N_4S$ requires: C, 50.57; H, 5.02; N, 10.72%.
Found: C, 50.54; H, 5.04; N, 10.69%.

EXAMPLE 3

1-(2,3,4,6-Tetra-O-acetyl-β-D-glucopyranosyl)-3-(benzothiazol-2-yl)-2-thiourea

To 10 ml of anhydrous xylene were added 390 mg (1 mmol) of 2,3,4,6-tetra-O-acetyl-D-glucopyranosyl isothiocyanate and 150 mg (1 mmol) of 2-aminobenzothiazole (MW 150) and the mixture was heated at 110° C for 40 minutes and allowed to cool to room temperature. Crystals formed were filtered off and recrystallized from methanol to give colourless needles melting between 179° and 181° C (uncorrected). Yield: 230 mg (42%).

IR $\nu_{max}^{KBr}$ cm$^{-1}$: 3300 (—NH), 1740 (COOCH$_3$), 1580, 750 (phenyl).

EXAMPLE 4

1-(4-Pyridylcarbonyl)-4-(2,3,4,6-tetra-O-acetyl-β-D-glucopyranosyl)-semicarbazide To 10 ml of anhydrous xylene were added 390 mg (1 mmol) of 2,3,4,6-tetra-O-acetyl-D-glucopyranosyl isothiocyanate and 140 mg (1 mmol) of isonicotinic acid hydrazide (MW 137) and the mixture was heated on an oil bath under reflux for 3 hours and allowed to cool to room temperature. Crystals formed were filtered off and recrystallized from methanol to give colourless needles melting between 140° and 142° C (uncorrected). Yield: 220 mg (42%).

IR $\nu_{max}^{KBr}$ cm$^{-1}$: 3300 (—NH), 1690 (CONH), 1600 (aromatic ring), 1740 (COOCH$_3$).

EXAMPLE 5

1-(2,3,4,6-Tetra-O-acetyl-β-D-glucopyranosyl)-3-(1,3-dimethylpyrimidin-2,4-dione-6-yl)-2-thiourea To 10 ml of anhydrous xylene were added 390 mg (1 mmol) of 2,3,4,6-tetra-O-acetyl-D-glucopyranosyl isothiocyanate and 140 mg (1 mmol) of 6-amino-1,3-dimethyluracil (MW 155) and the mixture was heated on an oil bath under reflux for 9–10 hours and allowed to cool to room temperature. Crystals formed were filtered off and recrystallized from ethanol to give colourless needles melting between 171° and 173° C (uncorrected). Yield: 240 mg (43%).

IR $\nu_{max}^{KBr}$ cm$^{-1}$: 3400 (—NH), 1740 (COOCH$_3$), 1700 (—N=C=S), 1380, 1370 (—CH$_3$).

EXAMPLE 6

Triethylammonium 6-(2,3,4,6-tetra-O-acetyl-β-D-glucopyranosyl-thioureido) penicillanate 0.5 ml of thriethylamine were added to a solution of 220 mg (1 mmol) of 6-amino-penicillanic acid (MW 216) in 0.7 ml of dimethylformamide maintained at 0° C and to this mixture was added a solution of 390 mg (1 mmol) of 2,3,4,6-tetra-O-acetyl-D-glucopyranosyl isothiocyanate in 0.2 ml of dimethylformamide. The mixture was stirred at 0°-5° C for 2 hours and then poured into 100 ml of ethylether. Crystals formed were filtered off and recrystallized from methanol to give colourless powdery crystals melting between 160° and 161° (uncorrected). Yield: 190 mg (32%).

IR $\nu_{max}^{KBr}$ cm$^{-1}$: 3350, 3250 (—NH), 1740 (COOCH$_3$),
1380, 1370 (gem—CH$_3$).

EXAMPLE 7

Triethylammonium α-(2,3,4,6-tetra-O-acetyl-β-D-glucopyranosylthioureido)-benzylpenicillinate The procedure of Example 6 was repeated except that a solution of 350 mg (1 mmol) of α-amino-benzylpenicillin (ampicillin) (MW 349) in 0.5 ml of dimethylformamide was used in place of the dimethylformamide solution of 6-amino-penicillanic acid, yielding a syrup. Yield: 200 mg (27%).

IR $\nu_{max}^{film}$ cm$^{-1}$: 3350 (—NH), 1740 (COOCH$_3$), 1380,
1370 (gem—CH$_3$).

EXAMPLE 8

1-(2,3,4,-tri-O-acetyl-α-D-arabinopyranosyl)-3-(benzothiazol-2-yl)-2-thiourea

To 15 ml of anhydrous xylene were added 320 mg (1 mmol) of 2,3,4-tri-O-acetyl-D-arabinopyranosyl isothiocyanate and 150 mg (1 mmol) of 2-aminobenzothiazole (MW 150) and the mixture was treated in the same manner as that used in Example 4, yielding a syrup. The syrup was purified by column chromatography on silica-gel using benzene-acetone as eluent to give the tilted compound from the fraction of benzene-acetone (9:1). Yield: 110 mg (24%).

IR $\nu_{max}^{film}$ cm$^{-1}$: 3300 (—NH), 1740 (COOCH$_3$), 1600,
760 (phenyl).

EXAMPLE 9

Triethylammonium 6-(2,3,4-tri-O-acetyl-α-D-arabinopyranosylthioureido) penicillanate The procedure of Example 6 was repeated using 320 mg (1 mmol) of 2,3,4-tri-O-acetyl-d-arabinopyranosyl isothiocyanate in place of 2,3,4,5-tetra-O-acetyl-D-glucopyranosyl isothiocyanate, yielding crystals. Yield: 215 mg (24%).

IR $_{max}^{KBr}$ cm$^{-1}$: 3250 (—NH), 1740 (COOCH$_3$), 1370,
1375 (gem—CH$_3$).

EXAMPLE 10

Triethylammonium α-(2,3,4,-tri-O-acetyl-α-D-arabinopyranosylthioureido) benzylpenicillinate The procedure of Example 7 was repeated using 320 mg (1 mmol) of 2,3,4-tri-O-acetyl-D-arabinopyranosyl isothiocyanate in place of 2,3,4,6-tetra-O-acetyl-D-glucopyranosyl isothiocyanate, yielding crystals. Yield: 240 mg (34%).

IR $_{max}^{KBr}$ cm$^{-1}$: 3350 (—NH), 1740 (COOCH$_3$), 1370,
1375 (gem—CH$_3$).

EXAMPLE 11

1-(2,3,4,6-Tetra-O-acetyl-β-D-glucopyranosyl)-3-(2,3-dimethyl-1-phenyl-3-pyrazolin-5-one-4-yl)-2-thiourea To 5 ml of anhydrous benzene were added 390 mg (1 mmol) of 2,3,4,6-tetra-O-acetyl-D-glucopyranosyl isothiocyanate and 200 mg (1 mmol) of 4-aminoantipyrine and the mixture was heated at 60°-70° C for 4 hours and allowed to cool to room temperature. Crystals formed were filtered off and recrystallized from petroleum ether to give pure crystals melting between 148° and 150° C (uncorrected). Yield: 300 mg (61%).

IR $_{max}^{KBr}$ cm$^{-1}$: 3350 (—NH), 1745 (COOCH$_3$).

EXAMPLE 12

1-(2,3,4-tri-O-acetyl-α-D-arabinopyranosyl)-3-(2,3-dimethyl-1-phenyl-3-pyrazolin-5-one-4-yl)-2-urea The procedure of Example 11 was repeated using 300 mg (1 mmol) of 2,3,4-tri-O-acetyl-D-arabinopyranosyl isocyanate (MW 301) in place of 2,3,4,6-tetra-O-acetyl-D-glucopyranosyl isothiocyanate, yielding crystals melting between 129° and 130° C (uncorrected). Yield: 320 mg (40%).

IR$_{max}^{KBr}$ cm$^{-1}$: 3280 (—NH), 1740 (COOCH$_3$) 1600, 750, 690 (phenyl).

EXAMPLE 13

α-(2,3,4-Tri-O-acetyl-α-D-arabinopyranosyl thioureido) benzylpenicillin

To 20 ml of anhydrous tetrahydrofuran were added 320 mg (1 mmol) of 2,3,4-tri-O-acetyl-D-arabinopyranosyl isothiocyanate and 350 mg (1 mmol) of ampicillin and the mixture was stirred at 5°-10° C for 4 days and then filtered. The solvent was distilled off under a reduced pressure and the residue was crystallized by the addition of ethylether. Recrystallization from tetrahydrofuran gave crystals melting between 178° and 179° C with decomposition (uncorrected). Yield: 610 mg (93%).

IR$_{max}^{KBr}$ cm$^{-1}$: 3350 (—NH), 1740 L (COOCH$_3$), 1600, 1500, 750 (aromatic ring).

Elementary analysis: $C_{28}H_{37}O_{11}N_4S_2$ requires: C, 50.21; H, 5.57; N, 8.36%. Found: C, 50.23; H, 5.52; N, 8.10%.

EXAMPLE 14

1-(2,3,4,5,6-Penta-O-acetyl-D-gluconyl)-3-(benzothiazol-2-yl)-2-thiourea

To 10 ml of anhydrous benzene were added 450 mg (1 mmol) of 2,3,4,5,6-penta-O-acetyl-D-gluconyl isothiocyanate and 150 mg (1 mmol) of 2-aminobenzothiazole and the mixture was heated on a water bath under reflux for 1 hour. After the solvent was distilled off under a reduced pressure, the residue was purified by column chromatography on silica gel using benzene-acetone as eluent to yield the titled compound from the fraction of benzene-acetone (3:1). Yield: 450 mg (75%).

IR$\nu_{max}$ $^{film}$ cm$^{-1}$: 3350, 3200 (—NH), 1740 (COOCH$_3$), 1605, 1590, 750 (phenyl).

Elementary analysis: $C_{24}H_{27}O_{11}N_3S_2$ requires: C, 48.24; H, 4.55; N, 7.03%. Found: C, 48.42; H, 4.62; N, 7.21%.

EXAMPLE 15

6-(2,3,4,5,6-Penta-O-acetyl-D-gluconyl thioureido) penicillanic acid

To 50 ml of anhydrous tetrahydrofuran were added 447 mg (1 mmol) of 2,3,4,5,6-penta-O-acetyl-D-gluconyl isothiocyanate and 216 mg (1 mmol) of 6-aminopenicillanic acid and the mixture was stirred at room temperature for 24 hours. The solvent was then distilled off under a reduced pressure and the residue was crystallized by the addition of dimethylformamide. Recrystallization from dimethylformamide gave colourless needles melting at 63° C (uncorrected). Yield: 630 mg (95%).

$IR\nu_{max}^{KBr}$ cm$^{-1}$: 3500 (—NH), 1790 ($\beta$-lactam), 1740 (COOCH$_3$), 3600 (—COOH).

Elementary analysis: $C_{25}H_{33}O_{14}N_3S_2$ requires: C, 45.20; H, 5.01; N, 6.33%. Found: C, 44.98; H, 5.46; N, 6.07%.

EXAMPLE 16

Phenacyl 6-(2,3,4,5,6-penta-O-acetyl-D-gluconyl thioureido) penicillanate

To 60 ml of anhydrous benzene were added 1.12 g (2.5 mmol) of 2,3,4,5,6-penta-O-acetyl-D-gluconyl isothiocyanate and 830 mg (2.5 mmol) of phenacyl 6-aminopenicillanate and the mixture was treated in the same manner as that used in Example 15. Recrystallization from ethylether gave colourless needles melting at 79° C (uncorrected). Yield: 760 mg (97%).

$IR\nu_{max}^{KBr}$ cm$^{-1}$: 3350 (—NH), 1790 ($\beta$-lactam), 1735 (COOCH$_3$), 1600 (phenyl).

Elementary analysis: $C_{33}H_{39}O_{15}N_3S_2$ requires: C, 50.69; H, 5.03; N, 5.37%. Found: C, 50.47; H, 5.24; N, 5.40%.

EXAMPLE 17

α-(2,3,4,5,6-Penta-O-acetyl-D-gluconyl-thioureido) benzylpenicillin

To 30 ml of anhydrous tetrahydrofuran were added 447 mg (1 mmol) of 2,3,4,5,6-penta-O-acetyl-D-gluconyl isothiocyanate and 376 mg (1 mmol) of ampicillin and the mixture was treated in the same manner as that used in Example 15. Yield: 780 mg (95%).

Rf: 0.63 (chloroform: methanol = 5:1).

$IR\nu_{max}^{KBr}$ cm$^{-1}$: 3550 (—COOH), 1740(COOCH$_3$), 700, 740 (phenyl).

EXAMPLE 18

1-(2,3,4,5,6-Penta-O-acetyl-D-gluconyl)-3-($\beta$-carboxy phenetyl-2-thiourea To 60 ml of anhydrous benzene were added 1.12 g (2.5 mmol) of 2,3,4,5,6-penta-O-acetyl-D-gluconyl isothiocyanate and 413 mg (2.5 mmol) of L-phenylalanine and the mixture was heated under reflux for 40 hours, after which 35 mg of unreacted L-phenylalanine were recovered. The solvent was then distilled off under a reduced pressure to give the titled compound. Yield: 520 mg (85%).

$IR\nu_{max}^{film}$ cm$^{-1}$: 3600 (—COOH), 1740 (COOCH$_3$), 1600, 750 (phenyl).

Elementary analysis: $C_{26}H_{32}O_{13}N_2S$ requires: C, 50.98; H, 5.27; N, 4.57%. Found: C, 50.72; H, 5.30; N, 4.60%.

EXAMPLE 19

1-phenyl-4-ethoxycarbonyl-5-(2,3,4,5,6-penta-O-acetyl-D-gluconylthioureido) pyrazole To 10 ml of anhydrous benzene were added 450 mg (1 mmol) of 2,3,4,5,6-penta-O-acetyl-D-gluconyl isothiocyanate and 230 mg (1 mmol) of ethyl 1-phenyl-5-aminopyrazol-4-carboxylate and the mixture was refluxed on a water bath for 10 hours, after which the solvent was distilled off under a reduced pressure. The residue was purified by column chromatography on silica gel using benzene-acetone as eluent to give the titled compound from the fraction of benzene-acetone (9:1). Yield: 580 mg (87%).

$IR\nu_{max}^{KBr}$ cm$^{-1}$: 3400 (—NH), 1740, 1700 (COOCH$_3$), 1590, 750 (phenyl).

Elementary analysis: $C_{28}H_{34}O_{13}N_4S$ requires: C, 50.45; H, 5.14; N, 8.40%. Found: C, 50.40; H, 5.42; N, 8.62%.

EXAMPLE 20

2-(2,3,4,5,6-Penta-O-acetyl-D-gluconylthioureido) pyridine

To 5 ml of anhydrous benzene were added 450 mg (1 mmol) of 2,3,4,5,6-penta-O-acetyl-D-gluconyl isothiocyanate and 94 mg (1 mmol) of 2-aminopyridine and the mixture was treated in the same manner as used in Example 19. Purification by column chromatography gave the titled compound from the fraction of benzene-acetone (48:2). Yield 445 mg (82%).

$IR\nu_{max}^{KBr}$ cm$^{-1}$: 3350 (—NH), 1740 (COOCH$_3$).

Elementary analysis: $C_{22}H_{27}O_{11}N_3S$ requires: C, 48.80; H, 5.03; N, 7.76%. Found: C, 48.68; H, 5.32; N, 7.56%.

EXAMPLE 21

1-phenyl-4-carbamoyl-5-(2,3,4,5,6-penta-O-acetyl-D-gluconylthioureido) pyrazole To 15 ml of anhydrous benzene were added 450 mg (1 mmol) of 2,3,4,5,6-penta-O-acetyl-D-gluconyl isothiocyanate and 200 mg (1 mmol) of 1-phenyl-5-aminopyrazol-4-carboxylic acid amide and the mixture was treated in the same manner as that used in Example 19. Purification by column chromatography gave the titled compound from the fraction of benzene-acetone (9:1). Yield: 5.06 mg (78%).

$IR\nu_{max}^{KBr}$ cm$^{-1}$: 3500 (—NH), 1740 (COOCH$_3$), 1640, 1590, 750 (phenyl).

Elementary analysis: $C_{27}H_{31}O_{12}N_5S$ requires: C, 49.92; H, 4.81; N, 10.78%. Found: C, 50.03; H, 4.78; N, 10.56%.

EXAMPLE 22

1-(4-Pyridylcarbonyl)-4-(2,3,4,5,6-penta-O-acetyl-D-gluconyl)-thiosemicarbazide To 10 ml of anhydrous benzene were added 450 mg (1 mmol) of 2,3,4,5,6-penta-O-acetyl-D-gluconyl isothiocyanate and 137 mg (1 mmol) of isonicotinic acid hydrazide and the mixture was treated in the same manner as used in Example 19. Purification by column chromatography gave the titled compound from the fraction of benzeneacetone (9:1). Yield: 470 mg (80%).

$IR\nu_{max}^{KBr}$ cm$^{-1}$: 3350, (—NH), 1740 (COOCH$_3$), 1700 (ketone).

Elementary analysis: $C_{23}H_{28}O_{12}N_4S$ requires: C, 47.26; H, 4.83; N, 9.58%. Found: C, 47.52; H, 4.78; N, 9.56%.

EXAMPLE 23

4-(2,3,4,5,6-Penta-O-acetyl-D-gluconylthioureido)-phenyl-N'-(3,4-dimethyl-5-isoxazolyl)-sulfonamide To 10 ml of anhydrous tetrahydrofuran were added 2.2 g (5 mmol) of 2,3,4,5,6-penta-O-acetyl-D-gluconyl isothiocyanate and 1.3 g (5 mmol) of sulfisoxazole and the mixture was stirred at room temperature for 24 hours. The solvent was distilled off under a reduced pressure to obtain the titled compound as residue. Yield: 3.2 g (92%).

Rf: 0.25 (silica gel; benzene:acetone = 4:1).

$IR\nu_{max}^{KB4}$ cm$^{-1}$: 3480 (—NH), 1740 (COOCH$_3$), 1550, 780 (aromatic ring).

Elementary analysis: $C_{28}H_{34}O_{14}N_4S_2$ requires: C, 47.05; H, 4.80; N, 7.84%. Found: C, 46.97; H, 4.72; N, 7.60%.

EXAMPLE 24

4-(2,3,4,5,6-Penta-O-acetyl-D-gluconylthioureido)-phenyl-N'-(2,6-dimethyl-4-pyrimidyl)-sulfonamide To 20 ml of anhydrous tetrahydrofuran was added 2.2 g (5 mmol) of 2,3,4,5,6-penta-O-acetyl-D-gluconyl isothiocyanate and 1.4 g (5 mmol) of sulfisomidin and the mixture was treated in the same manner as that used in Example 23 to yield a syrup. Crystallization from ethylether gave pale yellow needles melting between 125° and 126° C (uncorrected). Yield: 3.2 g (90%).

Rf: 0.58 (silica gel, chloroform: methanol= 9:1).

$IR\nu_{max}^{KBr}$ cm$^{-1}$: 3480 (—NH), 1740 (COOCH$_3$), 1600, 700 (aromatic ring).

Elementary analysis: $C_{29}H_{35}O_{13}N_5S_2$ requires: C, 47.99; H, 4.86; N, 9.65%. Found: C, 48.02; H, 4.74; N, 9.72%.

EXAMPLE 25

4-(2,3,4,5,6-Penta-O-acetyl-D-gluyconylthioureido)-phenyl-N'-(2-pyrimidyl)-sulfonamide To 10 ml of anhydrous tetrahydrofuran were added 4.4 g (10 mmol) of 2,3,4,5,6-penta-O-acetyl-D-gluconyl isothiocyanate and 2.5 g (10 mmol) of sulfadiazine and the mixture was treated in the same manner as that used in Example 23 to yield a syrup which was crystallized by the addition of ethylether. Recrystallization from ethanol-ethylether gave colourless needles melting between 100° and 112° (uncorrected). Yield: 6.5 g (95%).

Rf: 0.54 (silica gel, benzene:acetone = 3:2).

$IR\nu_{max}^{KBr}$ cm$^{-1}$: 3480 (—NH), 1740 (COOCH$_3$), 1580 (aromatic ring).

Elementary analysis:

$C_{27}H_{31}O_{13}N_5S_2$ requires: C, 46.48; H, 4.48, N, 10.04%.

Found: C, 46.72; H, 5.03; N, 10.21%.

EXAMPLE 26

4-(2,3,4,5,6-Penta-O-acetyl-D-gluconylthioureido)phenyl-N'-(2-thiazolyl)-sulfonamide To 20 ml of anhydrous tetrahydrofuran were added 4.4 g (10 mmol) of 2,3,4,5,6-penta-O-acetyl-D-gluconyl isothiocyanate and 2.5 g (10 mmol) of sulfathiazole and the mixture was treated in the same manner as that used in Example 23 to yield a syrup which was crystallized by the addition of ethylether. Recrystallization from benzene-ethylether gave pale yellow needles melting between 123° and 124° C (uncorrected). Yield: 6.3 g (90%).

$IR\nu_{max}^{KBr}$ cm$^{-1}$: 3480 (—NH), 1740 (COOCH$_3$), 1580 (aromatic ring).

Elementary analysis:

$C_{26}H_{30}O_{13}N_4S_3$ requires: C, 44.44; H, 4.30; N, 7.97%.

Found: C, 44.02, H, 4.32; N, 7.74%.

EXAMPLE 27

4-(2,3,4,5,6-Penta-O-acetyl-D-gluconylthioureidomethyl)-phenyl-sulfonamide

An aqueous ammonia was added to an aqueous solution containing 5 g of homosulfamine, when colourless needles were deposited and filtered off. The needles were dried over silica gel under a reduced pressure, yielding 4.5 g of free homosulfamine.

To 20 ml of anhydrous tetrahydrofuran were added 1.8 g (10 mmol) of the free homosulfamine and 4.4 g (10 mmol) of 2,3,4,5,6-penta-O-acetyl-D-gluconyl isothiocyanate and the mixture was treated in the same manner as that used in Example 23 to yield crystals. Recrystallization from tetrahydrofuran-ethylether gave colourless needles melting between 119° and 120° C (uncorrected). Yield: 5.5 g (87%).

$IR\nu_{max}^{KBr}$ cm$^{-1}$: 3500, 3480 (—NH$_2$, —NH), 1740 (COOCH$_3$), 1580, 780 (aromatic ring).

Elementary analysis:

$C_{24}H_{31}O_{13}N_3S_2$ requires: C, 45.50; H, 4.93; N, 6.63%. Found: C, 45,32; H, 4.73; N, 6.50%.

EXAMPLE 28

7-[D-α-(2,3,4,5,6-penta-O-acetyl-D-gluconyl thioureido)-phenylacetamido]-3-methyl-3-cephem-4-carboxylic acid To 20 ml of anhydrous tetrahydrofuran were added 2.2 g (5 mmol) of 2,3,4,5,6-penta-O-acetyl-D-gluconyl isothiocyanate and 1.2 g (5 mmol) of cephalexin and the mixture was stirred at room temperature for 3 days and filtered. The filtrate was concentrated under a reduced pressure and crystallized by the addition of ehtylether. Recrystallization from tetrahydrofuran-ethylether gave crystals melting between 134° and 136° C (uncorrected). Yield: 3.4 g (87%).

Rf: 0.46 (silica gel, chloroform:methanol = 9:1).

$IR\nu_{max}^{KBr}$cm$^{-1}$: 3200 (—NH), 1740 (COOCH$_3$), 730, 700, 695 (phenyl).

Elementary analysis:

$C_{33}H_{38}O_{15}N_4S_2$ requires: C, 49.87; H, 4.82; N, 7.05%. Found: C, 49.85; H, 4.80; N, 7.20%.

EXAMPLE 29

2,3,4,5,6,-Penta-O-acetyl-D-gluconyl isothiocyanate

This example illustrates the preparation of a compound of the formula II, starting material of the process of this invention, which is in itself novel.

To 200 ml of anhydrous xylene were added 9.0 g (20 mmol) of 2,3,4,5,6-penta-O-acetyl-D-gluconyl chloride which was prepared by the method proposed by R. T. Major and E. W. Cook [J. Am. Chem. Soc., 58, 2474 (1936)]. 3.3 g of silver thiocyanate were added to the mixture in a dry nitrogen stream under stirring and the reaction mixture was heated at 90°–100° C for 1 hour, after which further 1.7 g of silver thiocyanate were added thereto and the heating was continued for further 5 hours. The reaction mixture was then allowed to cool to room temperature and poured into 300 ml of petroleum ether to form colourless needles. Yield: 8.2 g (92%).

IR$\nu_{max}^{KBr}$ cm$^{-1}$: 1980 (NCS), 1740 (COOCH$_3$).

Elementary analysis:
C$_{17}$H$_{21}$O$_{11}$NS requires: C, 45.64; H, 4.73; N, 3.13%.
Found: C, 45.59; H, 4.70; N, 3.09%.

What we claim is:

1. Sugar ureide and thioureide derivatives of the formula:

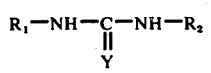

wherein R$_1$ represents glucopyranosyl, arabinopyranosyl or gluconyl whose alcoholic hydroxyl groups have been protected by HO-protecting groups; α-(3-carboxy-2,2-dimethylpenam-6-yl-aminocarbonyl)benzyl, α-(4-carboxy-3-methyl-3-cephem-7-yl-aminocarbonyl)benzyl, 2-pyridyl, 2-benzimidazolyl, 2-benzothiazolyl, 6-(1,3-dimethyl-2,4-dioxo)-pyrimidinyl, 5-(4-carbamoyl-1-phenyl)pyrazolyl, 5-(4-ethoxycarbonyl-1-phenyl)pyrazolyl, 4-(2,3-dimethyl-5-oxo-1-phenyl)pyrazolinyl, 6-penicillanyl, 6-(3-phenacyl)-penicillanyl, isonicotinoylamino, p-[N-3,4-dimethyl]-5-isoxazolyl]sulfamoylphenyl, p-[N-(2,6--dimethyl)-4-pyrimidinyl]sulfamoylphenyl, p-(N-2-pyrimidinyl)-sulfamoylphenyl or p-(N-2-thiazolyl)sulfamoylphenyl; and Y represents an atom of oxygen or sulfur.

2. Compounds as claimed in claim 1, in which the HO-protecting groups are acetyl.

3. Compounds as claimed in claim 1 in which the OH-protecting groups are selected from benzoyl, benzyl, isopropylidene, benzylidene and cyclohexylidene.

4. Compounds as claimed in claim 1 in which the group R$_1$ is 2,3,4,6-tetra-O-acetyl-D-glucopyranosyl group.

5. Compounds as claimed in claim 1 in which the group R$_1$ is 2,3,4-tri-O-acetyl-D-arabinopyranosyl group.

6. Compounds as claimed in claim 1 in which the group R$_1$ is 2,3,4,5,6-penta-O-acetyl-D-gluconyl group.

7. α-(2,3,4,6-Tetra-O-acetyl-D-glucopyranosylthioureido) benzylpenicillin and triethylammonium salt thereof.

8. α-(2,3,4-Tri-O-acetyl-D-arabinopyranosylthioureido) benzylpenicillin and triethylammonium salt thereof.

9. α-(2,3,4,5,6-Penta-O-acetyl-D-gluconylthioureido) benzylpenicillin and triethylammonium salt thereof.

10. 7-[D-α-(2,3,4,5,6-penta-O-acetyl-D-gluconylthioureido)-phenylacetamido]-3-methyl-3-cephem-4-carboxylic acid.

11. Compounds selected from:
1-(2,3,4,6-Tetra-O-acetyl-β-D-glucopyranosyl)-3-(benzimidazol-2-yl)-2-thiourea;
1-(2,3,4,6-Tetra-O-acetyl-β-D-glucopyranosyl)-3-(benzothiazol-2-yl)-2-thiourea;
1-(4-Pyridylcarbonyl)-4-(2,3,4,6-tetra-O-acetyl-β-D-glucopyranosyl)-semicarbazide;
1-(2,3,4,6-Tetra-O-acetyl-β-D-glucopyranosyl)-3-(1,3-dimethylpyrimidin-2,4-dione-6-yl)-2-thiourea;
6-(2,3,4,6-Tetra-O-acetyl-β-D-glucopyranosylthioureido) penicillanic acid and its triethylammonium salt;
1-(2,3,4-Tri-O-acetyl-α-D-arabinopyranosyl)-3-(benzothiazol-2-yl)-2-thiourea;
6-(2,3,4-Tri-O-acetyl-α-D-arabinopyranosyl-thioureido) penicillanic acid and its triethylammonium salt;
1(2,3,4,6-Tetra-O-acetyl-β-D-glucopyranosyl)-3-(2,3-dimethyl-1-phenyl-3-pyrazolin-5-one-4-yl)-2-thiourea;
1-(2,3,4-Tri-O-acetyl-α-D-arabinopyranosyl)-3-(2,3-dimethyl-1-phenyl-3-pyrazolin-5-one-4yl)-2-urea;
1-(2,3,4,5,6-Penta-O-acetyl-D-gluconyl)-3-(benzothiazol-2-yl)-2-thiourea;
6-(2,3,4,5,6-Penta-O-acetyl-D-gluconyl-thioureido) penicillanic acid and its phenacyl ester;
1-(2,3,4,5,6-Penta-O-acetyl-D-gluconyl)-3-(β-carboxy phenetyl)-2-thiourea;
1-Phenyl-4-ethoxycarbonyl-5-(2,3,4,5,6-penta-O-acetyl-D-gluconylthioureido) pyrazole;
2-(2,3,4,5,6-Penta-O-acetyl-D-gluconylthioureido) pyridine;
1-Phenyl-4-carbamoyl-5-(2,3,4,5,6-penta-O-acetyl-D-gluconylthioureido) pyrazole;
1-(4-Pyridylcarbonyl)-4-(2,3,4,5,6-penta-O-acetyl-D-gluconyl)-thiosemicarbazide;
4-(2,3,4,5,6-Penta-O-acetyl-D-gluconylthioureido)-phenyl-N'-(3,4-dimethyl-5-isoxazolyl)-sulfonamide;
4-(2,3,4,5,6-Penta-O-acetyl-D-gluconylthioureido)-phenyl-N'-(2,6-dimethyl-4-pyrimidyl)-sulfonamide; 4-(2,3,4,5,6-Penta-O-acetyl-D-gluconylthioureido)-phenyl-N'-(2-pyrimidyl)-sulfonamide;
4-(2,3,4,5,6-Penta-O-acetyl-D-gluconylthioureidophenyl-N'-(2-thiazolyl)-sulfonamide; and
4-(2,3,4,5,6-Penta-O-acetyl-D-gluconylthioureidomethyl)phenyl-sulfonamide.

12. A pharmaceutical composition comprising an effective amount of a sugar ureide or thioureide derivative as claimed in claim 1 in association with a pharmaceutical carrier or diluent.

13. A composition as claimed in claim 12 in a form suitable for oral administration.

14. A method for therapeutic treatment of bacterial infections which comprises orally and parenterally administering to a patient infected with gram-positive or gram-negative bacteria a therapeutically effective amount, at suitable intervals, of a sugar ureide or thioureide derivative as claimed in claim 1 in the form of a pharmaceutical preparation.

15. Sugar ureide and thioureide derivatives of the formula:

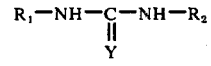

wherein R$_1$ represents glucopyranosyl, arabinopyranosyl or gluconyl whose alcoholic hydroxyl groups have been protected by HO-protected groups; R$_2$ represents p-sulfamoyl-benzyl, α-(3-carboxy-2,2-dimethylpenam-6-yl-aminocarbonyl)benzyl, α-(4-carboxy-3-methyl-3-cephem-7-yl-aminocarbonyl)benzyl, 2-benzimidazoyl, 2-benzothiazolyl, 6-(1,3-dimethyl-2,4-dioxo)pyrimidinyl, 5-(4-carbamoyl-1-phenyl)pyrazolyl, 5-(4-ethoxycarbonyl-1-phenyl)pyrazolyl, 4-(2,3-dimethyl-5-oxo-1-phenyl)pyrazolinyl, 6-penicillanyl, 6-(3-phenacyl)penicillanyl, isonicotinoylamino, p-[N-3,4-dimethyl)-5-isoxazolyl]sulfamoyl-phenyl, p-[N-(2,6-dimethyl)-4-pyrimidinyl]sulfamoylphenyl, p-(N-2-pyrimidinyl)sulfamoylphenyl or p-(N-2-thiazolyl)sulfamoylphenyl; and Y represents an atom of oxygen or sulfur.

16. Sugar ureide and thioureide derivatives of the formula:

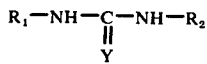

wherein $R_1$ represents glucopyranosyl whose alcoholic hydroxyl groups have been protected by HO-protected groups; $R_2$ represents α-(3-carboxy-2,2-dimethylpenam-6-yl-aminocarbonyl)benzyl, 2-benzimidazolyl, 2-benzothiazolyl, 6-(1,3-dimethyl-2,4-dioxo(pyrimidinyl, 4-(2,3-dimethyl-5-oxo-1-phenyl)pyrazolinyl, 6-penicillanyl or isonicotinoylamino, and Y represents an atom of oxygen or sulfur.

17. Sugar ureide and thioureide derivatives of the formula:

wherein $R_1$ represents arabinopyranosyl whose alcoholic hydroxyl groups have been protected by HO-Protecting groups; $R_2$ represents α-(3-carboxy-2-dimethylpenam-6-yl-aminocarbonyl)benzyl, 2-benzothiazolyl or 4-(2,3-dimethyl-5-oxo-1-phenyl)pyrazolinyl; and Y represents an atom of oxygen or sulfur.

18. As novel compounds sugar ureide and thioureide derivatives of the general formula:

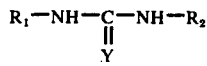

wherein $R_1$ represents gluconyl group of which the alcoholic hydroxyl groups have been protected; $R_2$ represents β-carboxyphentyl, p-sulfamoyl-benzyl, α-(3-carboxy-2,2-dimethyl-penam-6-yl-aminocarbonyl)benzyl, α-(4-carboxy-3-methyl-3-cephem-7-yl-aminocarbonyl)benzyl, 2-pyridyl, 2-benzothiazolyl, 5-(4-carbamoyl-1-phenyl)pyrazolyl, 5-(4-ethoxycarbonyl-1-phenyl)pyrazolyl, 6-penicillanyl, 6-(3-phenacyl)-penicillanyl, isonicotinoylamino, p-[N-(3,4-dimethyl)-5-isoxazolyl]sulfamoylphenyl, p-[N-(2,6-dimethyl)4-pyrimidinyl]sulfamoylphenyl, p-(N-2-pyrimidinyl)sulfamoylphenyl or p-(N-2-thiazolyl) sulfamoylphenyl group; and Y represents an atom of oxygen or sulfur.

* * * * *

UNITED STATES PATENT AND TRADEMARK OFFICE
CERTIFICATE OF CORRECTION

PATENT NO. : 4,025,622
DATED : May 24, 1977
INVENTOR(S) : OGURA ET AL

It is certified that error appears in the above-identified patent and that said Letters Patent are hereby corrected as shown below:

Claim 1, line 3 after the formula, after "HO-protecting groups"; insert, ...$R_2$ represents benzyl, $\beta$-carboxy-phenethyl, p-sulfamoyl-benzyl,...

Signed and Sealed this

Thirtieth Day of May 1978

[SEAL]

Attest:

RUTH C. MASON
Attesting Officer

LUTRELLE F. PARKER
Acting Commissioner of Patents and Trademarks